United States Patent
Webster et al.

(10) Patent No.: US 10,207,046 B2
(45) Date of Patent: Feb. 19, 2019

(54) ASEPTIC ASSEMBLING OF PHARMACEUTICAL CONTAINERS

(71) Applicant: Siemens Medical Solutions USA, Inc., Malvern, PA (US)

(72) Inventors: Eric Webster, Knoxville, TN (US); Steven Zigler, Knoxville, TN (US); Gregory James Simmons, Zeeland, MI (US)

(73) Assignees: Siemens Medical Solutions USA, Inc., Malvern, PA (US); B. Braun Medical Inc., Bethleham, PA (US)

( * ) Notice: Subject to any disclaimer, the term of this patent is extended or adjusted under 35 U.S.C. 154(b) by 218 days.

(21) Appl. No.: 15/250,961

(22) Filed: Aug. 30, 2016

(65) Prior Publication Data
US 2017/0088325 A1    Mar. 30, 2017

Related U.S. Application Data

(63) Continuation of application No. 14/868,576, filed on Sep. 29, 2015, now Pat. No. 9,456,956.

(51) Int. Cl.
*A61J 1/16* (2006.01)
*B65D 73/00* (2006.01)
*B65D 77/22* (2006.01)
*B65D 5/42* (2006.01)
*A61M 5/00* (2006.01)
(Continued)

(52) U.S. Cl.
CPC ............... *A61M 5/002* (2013.01); *A61J 1/16* (2013.01); *A61J 1/2065* (2015.05); *A61J 1/2089* (2013.01); *A61L 2/0035* (2013.01); *A61L 2/0094* (2013.01); *A61L 2/07* (2013.01); *A61L 2/081* (2013.01); *A61L 2/206* (2013.01); *A61L 2/26* (2013.01); *B65B 55/027* (2013.01); *B65D 73/0014* (2013.01); *B65D 77/22* (2013.01); *A61J 1/201* (2015.05); *A61J 1/2086* (2015.05);
(Continued)

(58) Field of Classification Search
CPC ......... B65D 73/0014; B65D 77/22; A61J 1/16
See application file for complete search history.

(56) References Cited

U.S. PATENT DOCUMENTS 3,340,671 A    9/1967   Loo
3,685,248 A    8/1972   Godelaine
(Continued)

FOREIGN PATENT DOCUMENTS

WO    2013092929    6/2013

OTHER PUBLICATIONS

International Search Report for Corresponding International Patent Application No. PCT/IB2016/01370, dated Apr. 7, 2017.

*Primary Examiner* — Adam Marcetich

(57) ABSTRACT

A template frame for holding a container and one or more additional components in a predetermined first arrangement is disclosed. The template frame has a first pair of stanchions for engaging the container; and additional pairs of stanchions provided for engaging the one or more additional components, wherein each of the additional pairs of stanchions is for engaging one of the one or more additional components, wherein the stanchions are arranged on the template frame for holding the container and the one or more additional components out of direct physical contact from one another in the predetermined first arrangement to be subsequently assembled into a second arrangement.

5 Claims, 3 Drawing Sheets

(51) Int. Cl.
  *A61J 1/20* (2006.01)
  *B65B 55/02* (2006.01)
  *A61L 2/00* (2006.01)
  *A61L 2/07* (2006.01)
  *A61L 2/08* (2006.01)
  *A61L 2/20* (2006.01)
  *A61L 2/26* (2006.01)
  *B65B 3/00* (2006.01)

(52) U.S. Cl.
  CPC ..... *A61L 2202/181* (2013.01); *A61L 2202/21* (2013.01); *A61L 2202/23* (2013.01); *B65B 3/003* (2013.01)

(56) References Cited

U.S. PATENT DOCUMENTS

| | | | |
|---|---|---|---|
| 3,696,920 A | 10/1972 | Lahay | |
| 3,822,783 A * | 7/1974 | Mortensen | B65D 73/0014 206/231 |
| 3,927,762 A | 12/1975 | Zdarsky et al. | |
| 4,023,678 A * | 5/1977 | Fiedler | A61F 6/14 206/363 |
| 5,102,408 A | 4/1992 | Hamacher | |
| 5,289,858 A | 3/1994 | Grabenkort | |
| 5,431,174 A | 7/1995 | Knute | |
| 5,601,730 A | 2/1997 | Page et al. | |
| 5,810,773 A | 9/1998 | Pesnicak | |
| 5,816,772 A | 10/1998 | Py | |
| 6,021,824 A | 2/2000 | Larsen et al. | |
| 6,162,199 A | 12/2000 | Geringer | |
| 6,497,697 B1 | 12/2002 | Cohn | |
| 7,744,580 B2 | 6/2010 | Reboul | |
| 8,002,737 B2 | 8/2011 | Tennican | |
| 9,456,956 B1 * | 10/2016 | Webster | A61J 1/2096 |
| 2002/0095121 A1 | 7/2002 | Norton et al. | |
| 2003/0121811 A1 | 7/2003 | Roshdy | |
| 2004/0142562 A1 | 7/2004 | Chen et al. | |
| 2004/0158204 A1 | 8/2004 | Reboul | |
| 2004/0195145 A1 * | 10/2004 | Roshdy | A61B 50/33 206/570 |
| 2005/0194276 A1 * | 9/2005 | Lubs | A61M 25/002 206/364 |
| 2006/0079834 A1 * | 4/2006 | Tennican | A61J 1/2096 604/88 |
| 2008/0009789 A1 | 1/2008 | Zinger et al. | |
| 2009/0093757 A1 | 4/2009 | Tennican | |
| 2009/0194453 A1 | 8/2009 | Thorne et al. | |
| 2010/0300926 A1 * | 12/2010 | Specker | B65D 5/504 206/564 |
| 2011/0022023 A1 | 1/2011 | Weitzel et al. | |
| 2011/0155608 A1 | 6/2011 | Foster | |
| 2011/0297568 A1 * | 12/2011 | Miller | B65D 73/0014 206/375 |
| 2012/0199639 A1 * | 8/2012 | Given | B65D 5/5035 229/120.08 |
| 2012/0279899 A1 * | 11/2012 | Hsieh | B65D 5/5021 206/740 |
| 2013/0062245 A1 * | 3/2013 | Folchini | A61M 5/002 206/571 |
| 2013/0126389 A1 | 5/2013 | Holakovsky et al. | |
| 2013/0168277 A1 * | 7/2013 | Monti | B65D 5/48018 206/429 |
| 2013/0220484 A1 | 8/2013 | De Marco | |
| 2013/0225903 A1 | 8/2013 | Franci et al. | |
| 2013/0306509 A1 | 11/2013 | Caetano | |
| 2014/0259724 A1 | 9/2014 | McCarthy et al. | |
| 2014/0343553 A1 * | 11/2014 | Ford | A61B 17/1628 606/80 |
| 2014/0366486 A1 | 12/2014 | Hinz et al. | |
| 2015/0005734 A1 | 1/2015 | Fujio et al. | |
| 2016/0000650 A1 | 1/2016 | Frattini | |

* cited by examiner

ASEPTIC ASSEMBLING OF PHARMACEUTICAL CONTAINERS

CROSS-REFERENCE TO RELATED APPLICATIONS

This application is a continuation of the co-pending U.S. patent application Ser. No. 14/868,576, filed Sep. 29, 2015, the contents of which are incorporated herein by reference in its entirety.

FIELD

Aspects of the present disclosure relate in general to the preparation and handling of drug products that are administered as sterile solutions, and more particularly to sterile injectable drugs that are used in positron emission tomography (PET).

BACKGROUND

Aseptic processing is a technique that is used in several industries to make a finished drug product that is free of detectable microorganisms and/or toxic substances. Aseptic processing is typically performed in a controlled environment that is certified on a regular basis to standards set by the International Standards Organization (ISO), e.g. standard ISO 14644-1. This standard requires multiple layers of engineering and personnel controls including, operator training and qualifications, low particulate gowning, HEPA filter certification, specifically designed facilities, microbial environmental monitoring and trending, validated cleaning and disinfection procedures, and certified engineering controls that produce a certain level of particulate during operation. Conventionally, this issue is addressed by installing clean room environments and the associated procedures and policies that go along with a clean room environment. However, such solutions are costly.

SUMMARY

According to an aspect of the present disclosure, a sealed flexible pouch comprising the following provided inside the pouch is disclosed: a container for holding a pharmaceutical solution; one or more additional components for filling the container with the pharmaceutical solution; and a template frame holding the container and the one or more additional components in a predetermined first arrangement that allows the container and the one or more additional components to be assembled into a second arrangement without opening the sealed pouch. In some embodiments, the sealed flexible pouch is sterilized so the components within the sealed flexible pouch are sterilized and the interior of the sealed pouch provides an aseptic environment.

According to another aspect of the present disclosure, the container provided inside the sealed flexible pouch is pre-filled with a pharmaceutical solution and the one or more additional components would be components for withdrawing the pharmaceutical solution from the container. This embodiment would also include a template frame holding the container and the one or more additional components in a predetermined first arrangement that allows the container and the one or more additional components to be assembled into a second arrangement without opening the sealed pouch. In some embodiments, the flexible pouch including its contents is sterilized after the pouch is sealed so that the interior of the sealed pouch provides an aseptic environment.

According to another aspect, a method for preparing a sealed flexible pouch having an aseptic interior comprising the following provided inside the sealed flexible pouch is disclosed. The sealed pouch contains a container for holding a pharmaceutical solution; one or more additional components for subsequent process of the container; and a template frame holding the container and the one or more additional components in a predetermined first arrangement that allows the container and the one or more additional components to be assembled into a second arrangement without opening the sealed flexible pouch. The method comprises: (a) providing a flexible pouch having a sealable opening; (b) affixing the container and the one or more additional components to the template frame in the predetermined first arrangement; (c) placing the template frame inside the flexible pouch; (d) sealing the sealable opening of the flexible pouch; and (e) sterilizing the sealed flexible pouch whereby the components within the sealed flexible pouch are sterilized and the interior of the sealed flexible pouch provides an aseptic environment.

When the subsequent processing of the container involves filling the container with a pharmaceutical solution, the one or more additional components are those used for filling the container. In that embodiment, the container is empty when affixed to the template frame and placed inside the flexible pouch. Then, sometime after the sealed flexible pouch is sterilized, the container and the one or more additional components for filling the container can be aseptically assembled into the second arrangement, the sealed flexible pouch is unsealed open and then the container can be filled with a pharmaceutical solution.

In an embodiment where the container is pre-filled with a pharmaceutical solution and the subsequent processing of the container involves withdrawing and dispensing a pharmaceutical solution from the container, the one or more additional components are those used for withdrawing the pharmaceutical solution from the container. Such components can be a needle or a syringe, for example. In that embodiment, the container is pre-filled with the pharmaceutical solution and then affixed to the template frame and placed inside the flexible pouch. Then, sometime after the sealed flexible pouch is sterilized, the container and the one or more additional components for withdrawing and dispensing a pharmaceutical solution from the container can be aseptically assembled into the second arrangement, the sealed flexible pouch is unsealed open and then the pharmaceutical solution can be aseptically withdrawn from the container.

According to another aspect, a method for assembling a container and one or more additional components accompanying the container, all of which are provided inside a sealed flexible pouch having an aseptic interior is disclosed. The container and the one or more additional components are affixed to a template frame in a predetermined first configuration and provided inside the sealed flexible pouch. The method comprises: assembling the container and the one or more additional components into a second configuration without opening the sealed flexible pouch while the container and the one or more additional components remain inside the aseptic environment of the sealed flexible pouch. This method can be used to prepare the container to be filled with a pharmaceutical solution thereafter or the container can be pre-filled with a pharmaceutical solution and this method can be used to prepare the container for dispensing the pharmaceutical solution thereafter.

BRIEF DESCRIPTION OF THE DRAWINGS

All drawing figures are schematic and are not necessarily to scale.

DETAILED DESCRIPTION

This description of the exemplary embodiments is intended to be read in connection with the accompanying drawings, which are to be considered part of the entire written description.

This disclosure describes an invention that allows for conducting an aseptic operation, such as aseptic assembly of components, within a sterile microenvironment provided by a sealed flexible pouch which eliminates the need for installing a clean room environment for carrying out the aseptic operation. One example of industrial application for the present invention is the PET drug manufacturing industry. PET drug manufacturers have been assembling final product vial assemblies in laminar flow hoods or clean rooms that require qualifications for personnel and equipment which are costly. The present invention would eliminate the need to use this equipment since the assembly of the final product vial assembly components can take place within an aseptic microenvironment provided by a sealed sterile pouch.

The concept presented in this disclosure is also useful outside of the PET drug manufacturing industry. When using injectable solutions, the end users at hospitals, compounding pharmacies, and physician offices typically insert pre-sterilized needles and syringes into a pre-sterilized container (e.g. a vial, a bag, etc.) that contains drug products for administration to patients. This is typically performed in open air which is not an aseptic environment and may lead to contamination of the drug product from the environment. The present invention would reduce the potential for contamination prior to delivery of the drug product to patients in such applications since the insertion of a dispensing device such as a needle, a syringe, or a dispensing spike into the drug product container would be performed within a sterile microenvironment provided inside a sealed pouch.

Figure 1:
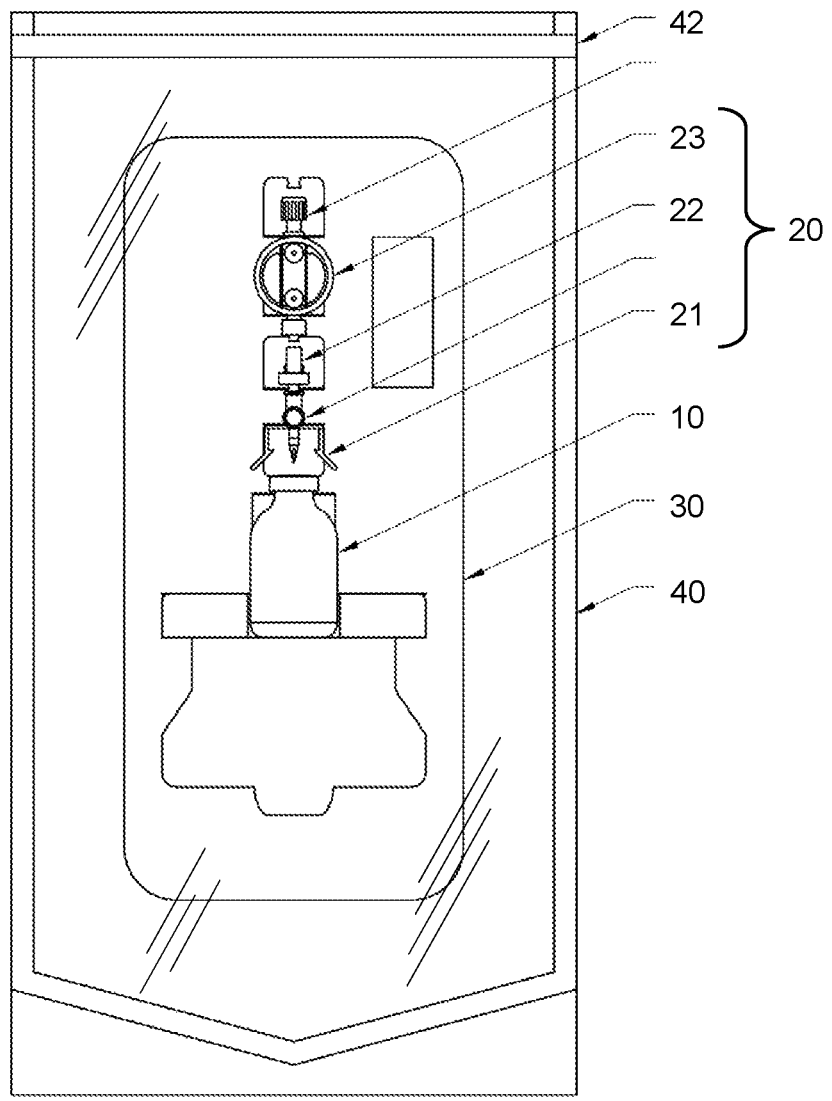
FIG. 1 shows a sealed flexible pouch with its contents: a container, one or more additional components, and a template frame holding the container and the one or more additional components, according to the present disclosure.

Referring to an example shown in FIG. 1, according to an aspect of the disclosure, a sealed flexible pouch 40 is provided. The sealed flexible pouch 40 contains a container 10, such as a vial, for holding a pharmaceutical solution; one or more additional components 20 for subsequent processing of the container; and a template frame 30. The template frame 30 holds the container 10 and the one or more additional components 20 in a predetermined first arrangement that allows the container and the one or more components to be assembled or reconfigured into a second arrangement without opening the sealed flexible pouch. The one or more additional components 20 can be any components that need to be assembled or reconfigured with the container 10 while they are still sealed inside the flexible pouch 40. In the illustrated example shown in FIG. 1, the one or more additional components 20 are a vented spike/needle 21 and a membrane filter 23. They are used for filling the container with a pharmaceutical solution. The vented spike/needle 21 is for puncturing a sealed closure on the container, such as a septum on a vial, to relieve pressure in the container during filling of the container. The vented spike/needle 21 has a valve portion 22 that is incorporated into the structure. The valve 22 can prevent backflow of the pharmaceutical liquid as the container is inverted for removal of the filtered pharmaceutical liquid. The valve 22 can provide a sterility barrier when the assembled container is removed from the flexible pouch 40. The membrane filter 23 used in the illustrated example for the pharmaceutical liquid is a sterilizing filter that sterilizes the pharmaceutical liquid as it flows through the filter during the process of filling the container 10.

Figure 2:
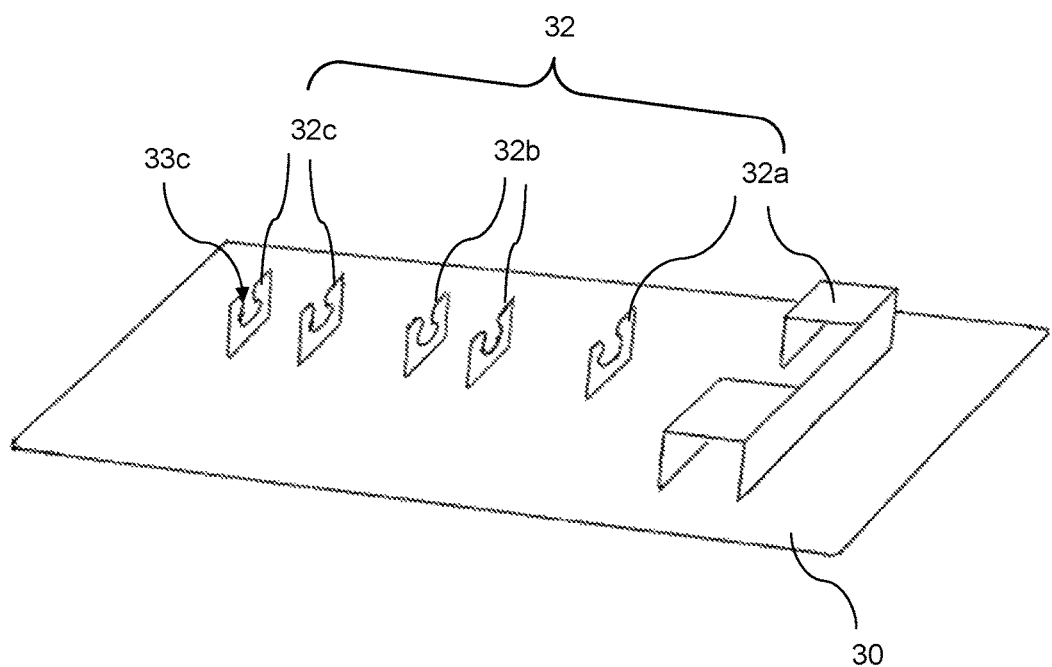
FIG. 2 shows the template frame alone.
Figure 3:
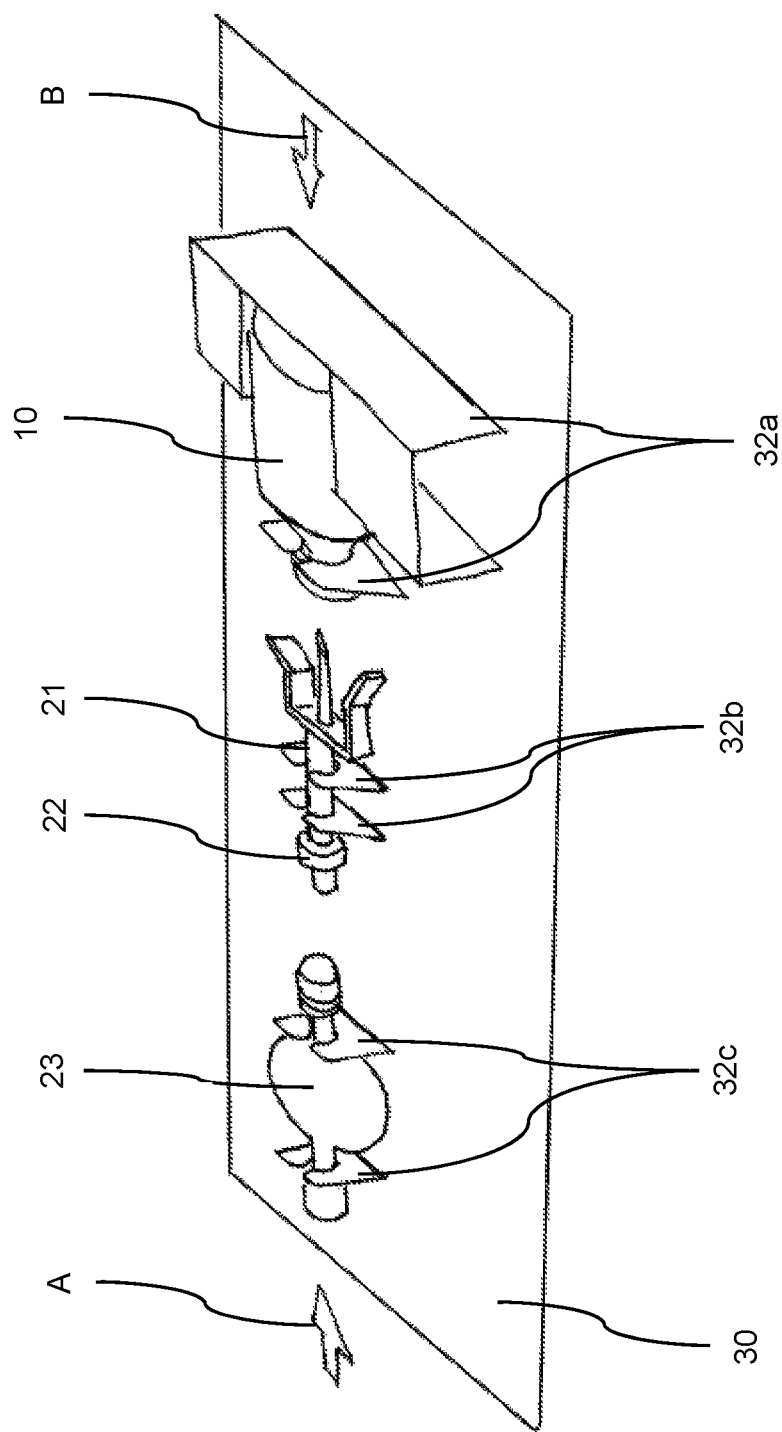
FIG. 3 shows the template frame with the container and one or more additional components affixed to the template frame in a predetermined first arrangement according to the present disclosure.

FIG. 2 shows the template frame 30 without the container 10 or the one or more additional components 20 fitted into the template frame 30. FIG. 3 shows the template frame 30 with the container 10 and the one or more additional components 20 fitted into the template frame in the predetermined first arrangement, wherein the container and the one or more additional components are held out of direct physical contact from one another. The template frame 30 is provided with an appropriate number of stanchions 32 that engage the one or more additional components 20 and hold the additional components in the predetermined first arrangement.

In the illustrated example of FIG. 2, the template frame 30 is provided with three pairs of stanchions 32a, 32b, 32c for engaging and holding the container 10, the vented spike/needle 21, and the membrane filter 23, respectively. In some embodiments, the one or more additional components 20 may include a greater or a fewer number of components, in which case, the template frame would then be provided with a correspondingly appropriate number of stanchions. The template frame can be made from a material that is sufficiently rigid such that when the container 10 and the one or more additional components are affixed to the template frame into the predetermined first arrangement, the template frame can maintain the container and the components in the first configuration. The stanchions 32 can be integrally formed out of the template frame 30 or the stanchions can be separate pieces attached to the template frame. In one example, the template frame 30 is formed from a sheet of rigid cardboard material and the integrally formed stanchions can be created by cutting the outline of the top portions of the stanchions in the template frame then folding the stanchion shapes up so that they stand up as shown. The base portion of the stanchions would be attached to the template frame. The template frame 30 and the stanchions 32 can be made of sufficiently rigid cardboard material, other heavy gauge paper-based material, plastic, composite material, metal, polymer, etc.

The stanchions 32 are configured to arrange their respective components, i.e., the container 10 and the additional components 20, in place in their predetermined first arrangement. The stanchions hold the components sufficiently snug so that the components will remain in the predetermined first arrangement during the shipping and handling of the sealed flexible pouch 40. For example, the stanchions 32a have cutout portions 33a along their top portions that are configured and shaped to hold the container 10 in place in the predetermined first arrangement. The stanchions 32b have cutout portions 33b along their top portions that are configured and shaped to hold the vented spike/needle 21 in place in the predetermined first arrangement. The stanchions 32c have cutout portions 33c along their top portions that are configured and shaped to hold the membrane filter 23 in place. The cutout portions of the stanchions are configured and shaped so that the respective additional components being held in place can be removed after the additional components are assembled into their second arrangement.

FIG. 3 shows the template frame 30 with the container 10, the vented spike/needle 21, and the membrane filter 23 fitted into their designated places in the predetermined first arrangement, wherein the container 10, the vented spike/needle 21, and the membrane filter 23 are held out of direct physical contact from one another. The container 10 engages the first pair of stanchions 32a, the vented spike/needle 21 engages the second pair of stanchions 32b, and the membrane filter 23 engages the third pair of stanchions 32c. In this example, the predetermined first arrangement involves having the container 10 and the one or more additional components 20 in a linear alignment as shown. The template frame 30 in this condition will be referred to herein as the "loaded state."

In the embodiment where the container 10 is pre-filled with a pharmaceutical solution and affixed to the template frame 30 along with one or more additional components for withdrawing the pharmaceutical solution from the container, the one or more additional component can be a syringe, for example. The syringe would be affixed to the template frame by a pair of stanchions so that the syringe and the container is in a predetermined first arrangement. In this first arrangement, the syringe is aligned with its needle directed toward the septum of the container 10. This arrangement is similar to the arrangement shown in FIG. 3 except that the vented spike/needle 21 would be replaced by a syringe. The second arrangement for this embodiment would be where the syringe's needle is inserted into the septum of the container.

In a preferred embodiment, the template frame 30 in its loaded state is placed inside the flexible pouch and hermetically sealed. The hermetic seal can be formed by any one of many methods known in the packaging art. In the illustrated example shown in FIG. 1, the flexible pouch is made of a heat sealable and preferably clear material such as plastic and is heat sealed. The heat sealed seal band 42 is shown in FIG. 1. The environment inside the flexible pouch can be simply air but can instead be filled with inert gas such as argon or nitrogen.

After the flexible pouch is sealed, the sealed flexible pouch 40 is sterilized so that the environment inside the sealed pouch 40 is aseptic. The sealed pouch 40 can be sterilized by ethylene oxide (EtO) gas, gamma radiation, steam, or other appropriate methods. In the case of EtO gas sterilization, the EtO gas permeate the sealed pouch 40 but not the container 10 which are typically glass or impermeable plastic. In steam sterilization, a small amount of a saline or water solution is placed into the pouch 40, seal the pouch 40, and then heated up to sterilize the components inside the pouch. Depending on the method of sterilization, ancillary components and/or reagents may be placed inside the flexible pouch prior to sealing in order to afford effective sterilization or to provide a visual indicator of the effectiveness of the sterilization process.

According to an aspect of the present disclosure, a method for forming the sealed flexible pouch 40 having an aseptic interior described above is disclosed. The method comprises:

(a) providing a flexible pouch having a sealable opening;
(b) affixing a container and the one or more additional components to a template frame in the predetermined first arrangement;
(c) placing the template frame inside the flexible pouch;
(d) sealing the sealable opening of the flexible pouch; and
(e) sterilizing the sealed flexible pouch.

In another embodiment, the method for forming the sealed flexible pouch having an aseptic interior can further include a step of placing ancillary components and/or reagents inside the flexible pouch after step (c) but before step (d).

In some embodiments, at least the steps (b), (c), and (d) are carried out in a cleanroom environment, either under a laminar flow hood or in a cleanroom. The cleanroom environment is at least ISO class 8 environment.

In some embodiments, the sterilizing of the sealed flexible pouch is carried out by EtO sterilization, gamma irradiation, or steam sterilization.

After the sealed pouch is sterilized, the components inside the sterile microenvironment in their first configuration can be manipulated and assembled into a second configuration without opening the pouch and compromising the aseptic integrity of the components.

After the components have been assembled into a second configuration, the pouch can be unsealed open and the assembled components can be used for the sterile filtration of the pharmaceutical solution into the container. Further manipulation of the components outside the pouch may be performed in a manner that does not compromise the aseptic integrity of the filtered pharmaceutical solution.

According to another aspect of the present disclosure, a method for assembling a container, such as a vial, for holding a pharmaceutical solution and one or more components for filling the container is disclosed. The container and the one or more additional components are affixed to a template frame in a predetermined first configuration and provided inside a sealed flexible pouch having an aseptic interior. In one example, the one or more additional components include a vented spike/needle for puncturing a sealed closure on the container, such as a septum on a vial, before filling the container with the pharmaceutical solution. The method comprises assembling the container and the one or more additional components into a second configuration without opening the sealed flexible pouch while the container and the one or more additional components remain in the aseptic environment of the sealed flexible pouch. The assembling includes inserting the vented spike/needle through the sealed closure on the container. In this example, the assembling process would involve pushing the components together in the directions represented by the arrows A and B in FIG. 3. The sealed pouch can then be unsealed open and the assembled container and the other components are removed from the flexible pouch for filling the container with a sterile pharmaceutical liquid.

According to the present disclosure, the template frame and the affixed container and the one or more additional components do not need to be sterilized before being placed in the pouch. The container and the other components are arranged on to the template frame in a manner that ensures component integrity during shipping and handling, and facilitates assembly of the components while remaining inside the sterile microenvironment of the sealed flexible pouch.

According to the present disclosure, the template frame and the affixed container and the one or more additional components may optionally be assembled and placed in the pouch in at least ISO class 8 conditions.

According to another aspect, the present invention can be useful in healthcare settings where sterile drug products such as injectable solutions are withdrawn from pre-filled vials or bags into sterile syringes before patient administration. According to the present disclosure, a medicine vial containing the sterile drug product is affixed to a template frame along with one or more additional components, such as a needle or a syringe, required to withdraw the sterile drug product. The medicine vial and the one or more additional components (e.g., a syringe) would be affixed to the template frame in a first arrangement and the whole assembly is placed inside a sealable flexible pouch. The pouch is then sealed and sterilized using the methods described above to sterilize interior environment of the sealed pouch as well as its contents. The end user, a nurse for example, can then assemble the medicine vial and the one or more additional components (a syringe in this example) into their second configuration by inserting the syringe into the septum of the medicine vial. This assembly can be carried out entirely through the sealed pouch without breaking the seal, thus, maintaining the aseptic environment provided by the sealed pouch.

The present invention provides a greater assurance of providing and maintaining sterility of the components before use; enables preparation of the components sealed in a sterile pouch at one location and ship them to a numerous end user locations where separate clean room environments do not need to be set up (i.e., eliminates the need for the use of laminar flow hoods and associated practices at the end user locations); greatly simplifies workflow and reduces cost at the end user facilities.

The apparatuses and processes are not limited to the specific embodiments described herein. In addition, components of each apparatus and each process can be practiced independent and separate from other components and processes described herein.

The previous description of embodiments is provided to enable any person skilled in the art to practice the disclosure. The various modifications to these embodiments will be readily apparent to those skilled in the art, and the generic principles defined herein may be applied to other embodiments without the use of inventive faculty. The present disclosure is not intended to be limited to the embodiments shown herein, but is to be accorded the widest scope consistent with the principles and novel features disclosed herein.

What is claimed is:

1. A template frame for holding a container and one or more additional components in a predetermined first arrangement, the template frame comprising:
   a first pair of stanchions configured for engaging and holding the container, wherein the first pair of stanchions have cutout portions along their top portions that are configured and shaped to hold the container in the predetermined first arrangement; and
   additional pairs of stanchions provided for engaging and holding the one or more additional components in the predetermined first arrangement, wherein the one or more additional components comprises a vented spike/needle for puncturing a sealed closure on the container, and a membrane filter for sterilizing a pharmaceutical liquid as the liquid flows through the filter;
   wherein one of the additional pairs of stanchions is configured for engaging and holding the vented spike/needle and have cutout portions along their top portions that are configured and shaped to hold the vented spike/needle;
   wherein another one of the additional pairs of stanchions is configured for engaging and holding the membrane filter and have cutout portions along their top portions that are configured and shaped to hold the membrane filter;
   wherein the stanchions are arranged on the template frame for holding the container and the one or more additional components out of direct physical contact from one another in the predetermined first arrangement to be subsequently assembled into a second arrangement; and
   wherein the stanchions are positioned on the template frame so that in the predetermined first arrangement, the container and the one or more additional components are in a linear alignment.

2. The template frame of claim 1, wherein the stanchions are separate pieces attached to the template frame.

3. The template frame of claim 1, wherein the stanchions are integrally formed from the template frame.

4. The template frame of claim 3, wherein each of the stanchions have a top portion for engaging the container or the one or more additional components, and a base portion, wherein the template frame is formed from a sheet of rigid cardboard material and the integrally formed stanchions are created by cutting an outline of the top portions of the stanchions in the template frame then standing the stanchions up by folding the stanchions up along the base portions.

5. The template frame of claim 1, wherein the template frame can be made from a material that is sufficiently rigid such that when the container and the one or more additional components are affixed to the template frame into the predetermined first arrangement, the template frame can maintain the container and the one or more components in the first arrangement.

* * * * *